(12) United States Patent
Zhu

(10) Patent No.: US 9,421,379 B2
(45) Date of Patent: Aug. 23, 2016

(54) NEUROMODULATION SYSTEM INCORPORATING MULTIVARIATE SENSING, MULTIVARIABLE PATTERN RECOGNITION, AND PATIENT SPECIFIC ADAPTATION

(71) Applicant: Boston Scientific Neuromodulation Corporation, Valencia, CA (US)

(72) Inventor: Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/607,188

(22) Filed: Jan. 28, 2015

(65) Prior Publication Data

US 2015/0238765 A1    Aug. 27, 2015

Related U.S. Application Data

(60) Provisional application No. 61/944,430, filed on Feb. 25, 2014.

(51) Int. Cl.

| | |
|---|---|
| *A61N 1/00* | (2006.01) |
| *A61N 1/36* | (2006.01) |
| *A61B 5/00* | (2006.01) |
| *A61B 5/11* | (2006.01) |
| *A61B 5/04* | (2006.01) |
| *A61N 1/372* | (2006.01) |

(52) U.S. Cl.
CPC ........ *A61N 1/36139* (2013.01); *A61B 5/04001* (2013.01); *A61B 5/1116* (2013.01); *A61B 5/1118* (2013.01); *A61B 5/407* (2013.01); *A61B 5/7264* (2013.01); *A61N 1/37217* (2013.01); *A61B 5/4836* (2013.01); *A61B 5/6867* (2013.01); *A61N 1/36071* (2013.01); *A61N 1/37235* (2013.01)

(58) Field of Classification Search
CPC .......... A61N 1/36139; A61N 1/37217; A61B 5/04001; A61B 5/1116; A61B 5/1118; A61B 5/407; A61B 5/7264
See application file for complete search history.

(56) References Cited

U.S. PATENT DOCUMENTS

| | | | |
|---|---|---|---|
| 6,516,227 | B1 | 2/2003 | Meadows et al. |
| 6,895,280 | B2 | 5/2005 | Meadows et al. |
| 6,993,384 | B2 | 1/2006 | Bradley et al. |
| 7,239,920 | B1 | 7/2007 | Thacker et al. |
| 7,317,948 | B1 | 1/2008 | King et al. |
| 7,539,538 | B2 | 5/2009 | Parramon et al. |
| 7,650,184 | B2 | 1/2010 | Walter |
| 7,684,869 | B2 | 3/2010 | Bradley et al. |

(Continued)

*Primary Examiner* — Scott Getzow
(74) *Attorney, Agent, or Firm* — Schwegman Lundberg & Woessner, P.A.

(57) ABSTRACT

A medical system configured for performing a medical function in a patient. The medical system comprises at least one medical lead configured for being implanted adjacent a tissue region of the patient, at least one sensing element, monitoring circuitry configured for acquiring a plurality of physiological measurements from the sensing element(s) during one of a plurality of events respectively corresponding to a plurality of classes, and a processor configured for deriving a set of data from the plurality of physiological measurements, performing a feature extraction technique on the data set to acquire at least one feature, analyzing the feature(s), and classifying the data set into the one class corresponding to the one event. The medical system further comprises a controller configured for performing a function based on the classified data set.

20 Claims, 9 Drawing Sheets

(56) References Cited

U.S. PATENT DOCUMENTS

| | | |
|---|---|---|
| 7,742,823 B2 | 6/2010 | King et al. |
| 7,831,307 B1 | 11/2010 | Moffitt |
| 7,853,330 B2 | 12/2010 | Bradley et al. |
| 8,019,439 B2 | 9/2011 | Kuzma et al. |
| 8,131,357 B2 | 3/2012 | Bradley et al. |
| 8,233,992 B2 | 7/2012 | Zhu et al. |
| 8,380,301 B2 | 2/2013 | Zhu |
| 8,401,665 B2 | 3/2013 | Bradley et al. |
| 8,594,785 B2 | 11/2013 | Bradley |
| 2003/0139781 A1 | 7/2003 | Bradley et al. |
| 2010/0305631 A1 | 12/2010 | Bradley et al. |
| 2010/0331922 A1 | 12/2010 | DiGiore et al. |
| 2012/0232614 A1* | 9/2012 | Bloemer ............ A61N 1/36128 607/46 |
| 2012/0265279 A1 | 10/2012 | Zhu |

\* cited by examiner

NEUROMODULATION SYSTEM INCORPORATING MULTIVARIATE SENSING, MULTIVARIABLE PATTERN RECOGNITION, AND PATIENT SPECIFIC ADAPTATION

CLAIM OF PRIORITY

This application claims the benefit of priority under 35 U.S.C. §119(e) of U.S. Provisional Patent Application Ser. No. 61/944,430, filed on Feb. 25, 2014, which is herein incorporated by reference in its entirety.

FIELD OF THE INVENTION

The present invention relates to implantable medical systems, and more particularly, to apparatus and methods for sensing the local physiological environment of tissue in which electrical medical leads are implanted.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, Functional Electrical Stimulation (FES) systems have been applied to restore some functionality to paralyzed extremities in spinal cord injury patients. Furthermore, in recent investigations Peripheral Nerve Stimulation (PNS) systems have demonstrated efficacy in the treatment of chronic pain syndromes and incontinence, and a number of additional applications are currently under investigation. Occipital Nerve Stimulation (ONS), in which leads are implanted in the tissue over the occipital nerves, has shown promise as a treatment for various headaches, including migraine headaches, cluster headaches, and cervicogenic headaches.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. Thus, electrical pulses can be delivered from the neurostimulator to the neurostimulation leads to stimulate the tissue and provide the desired efficacious therapy to the patient. The neurostimulation system may further comprise a handheld patient programmer in the form of a remote control (RC) to remotely instruct the neurostimulator to generate electrical stimulation pulses in accordance with selected stimulation parameters. A typical stimulation parameter set may include the electrodes that are acting as anodes or cathodes, as well as the amplitude, duration, and rate of the stimulation pulses.

Thus, the RC can be used to instruct the neurostimulator to generate electrical stimulation pulses in accordance with the selected stimulation parameters. Typically, the stimulation parameters programmed into the neurostimulator can be adjusted by manipulating controls on the RC to modify the electrical stimulation provided by the neurostimulator system to the patient. Thus, in accordance with the stimulation parameters programmed by the RC, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

The IPG may be programmed by a clinician, for example, by using a clinician's programmer (CP), which typically includes a general purpose computer, such as a laptop, with a programming software package installed thereon. Typically, the RC can only control the neurostimulator in a limited manner (e.g., by only selecting a program or adjusting the pulse amplitude or pulse width), whereas the CP can be used to control all of the stimulation parameters, including which electrodes are cathodes or anodes.

In the context of an SCS procedure, one or more stimulation leads are introduced through the patient's back into the epidural space, such that the electrodes carried by the leads are arranged in a desired pattern and spacing to create an electrode array. One type of commercially available stimulation leads is a percutaneous lead, which comprises a cylindrical body with ring electrodes, and can be introduced into contact with the affected spinal tissue through a Touhy-like needle, which passes through the skin, between the desired vertebrae, and into the epidural space above the dura layer. After proper placement of the neurostimulation leads at the target area of the spinal cord, the leads are anchored in place at an exit site to prevent movement of the neurostimulation leads.

To facilitate the location of the neurostimulator away from the exit point of the neurostimulation leads, lead extensions are sometimes used. The neurostimulation leads, or the lead extensions, are then connected to the IPG, which can then be operated to generate electrical pulses that are delivered, through the electrodes, to the targeted tissue, and in particular, the dorsal column and dorsal root fibers within the spinal cord. Intra-operatively (i.e., during the surgical procedure), the neurostimulator may be operated to test the effect of stimulation and adjust the parameters of the stimulation for optimal pain relief. A computer program, such as Bionic Navigator®, available from Boston Scientific Neuromodulation Corporation, can be incorporated in a clinician's programmer (CP) (briefly discussed above) to facilitate selection of the stimulation parameters. Any incisions are then closed to fully implant the system. Post-operatively (i.e., after the surgical procedure has been completed), a clinician can adjust the stimulation parameters using the computerized programming system to re-optimize the therapy.

After implantation of the neurostimulation leads, it may be desirable to electrically monitor the physiological environment in which the neurostimulation leads have been implanted in order to perform any one of various functions.

For example, the efficacy of SCS is related to the ability to stimulate the spinal cord tissue that innervates the region of pain experienced by the patient. Thus, the working clinical paradigm is that achievement of an effective result from SCS depends on the neurostimulation lead or leads being placed in a location (both longitudinal, lateral, and depth) relative to the spinal tissue, such that the electrical stimulation will treat the region of pain (i.e., the target of treatment). If a lead is not correctly positioned, it is possible that the patient will receive little or no benefit from an implanted SCS system. Thus, correct lead placement can mean the difference between effective and ineffective pain therapy, and as such, precise positioning of the leads proximal to the targets of stimulation is critical to the success of the therapy.

For example, multi-lead configurations, which enable more programming options for optimizing therapy, have been increasingly used in SCS applications. The use of multiple leads that are grouped together in close proximity to each other at one general region of the patient (e.g., side-by-side parallel leads along the spinal cord of the patient), increases the stimulation area and penetration depth (therefore coverage), as well as enables more combinations of anodic and cathodic electrodes for stimulation, such as transverse multipolar (bipolar, tripolar, or quadra-polar) stimulation, in addition to any longitudinal single lead configuration. Furthermore, with these lead configurations, current can be manipulated between leads medio-laterally to create the desired stimulation field. The resulting stimulation field is highly dependent on the relative position of the electrodes selected for stimulation.

Although the neurostimulation lead(s) may initially be correctly positioned relative to each other or relative to the stimulation target(s), the neurostimulation lead(s) are at risk of migration relative to each other and/or relative to the stimulation target(s). The neurostimulation lead(s) may migrate both acutely (e.g., during posture change or during activity/exercise) or chronically. In the context of SCS, the neurostimulation lead(s) may potentially migrate in three dimensions: rostro-caudally (along the axis of the spinal cord), medio-laterally (lateral to the spinal cord), and dorsal-ventrally (depth of the lead relative to the spinal cord). Notably, because the thickness of the cerebral spinal fluid (CSF) between the neurostimulation lead(s) and the spinal cord vary along the length spinal cord, migration of the neurostimulation lead(s) in the rostro-caudal direction may necessarily in the lead(s) being subjected to a different volume of CSF. Once the leads(s) migrate from their original position, a corrective action, such as surgical repositioning or electronic reprogramming of the neurostimulation leads may need to be performed relocate the stimulation to the targeted tissue region. Further details discussing the detection of lead migration by measuring electrical parameters, such as impedance, field potential, and evoked action potentials, are provided in U.S. Pat. Nos. 7,684,869, 7,853,330, and 8,401,665, which are expressly incorporated herein by reference.

As another example of a reason for electrically monitoring the physiological environment of the neurostimulation leads is that the coupling efficiency between the active electrodes and the targeted tissue region may change (either increase or decrease) as a result of inherent changes in the tissue characteristics typically caused by the tissue encapsulation process, which eventually surrounds the neurostimulation lead(s) with fibrous collagenous tissue (i.e., scar tissue) in an attempt to isolate the foreign materials of the neurostimulation lead(s). If the coupling efficiency decreases as a result of the tissue encapsulation process (or other processes), the intensity of the stimulation may be too low to provide effective therapy, whereas if the coupling efficiency increases as a result of the tissue encapsulation process (or other processes), the intensity of the stimulation may be too high and may overstimulate the targeted tissue region, inadvertently stimulate non-targeted tissue, and/or waste energy. Thus, knowledge of the coupling efficiency between the electrodes and the target tissue will allow the intensity of the stimulation to be adjusted to provide for a safe and efficacious level of therapy. In one preferred embodiment, the impedance between the electrodes and the target tissue is measured to determine the coupling efficiency, such that the amplitude of the stimulation can be automatically adjusted, as described in U.S. Pat. No. 7,742,823, which is expressly incorporated herein by reference.

In addition to tracking the coupling efficiency between the electrodes and the target tissue, it may be desirable to provide insight into the state of the encapsulation process (e.g., if the scar tissue has matured, is developing, is nascent, or even absent, etc.), thereby providing an indication of the stability of the neurostimulation lead(s). For example, if the encapsulation process is in the early stages, the activity of the patient may be limited so that the encapsulation process is not disrupted. In contrast, if the encapsulation process is complete, the neurostimulation lead(s) may be stabilized, and thus, no physical limitations may be placed on the patient.

As still another example of a reason for electrically monitoring the physiological environment of the neurostimulation leads is that it may be desirable to track the physical activity (e.g., activity level or body manipulations) of the patient that has received the implantable neurostimulation system, which provides an indication of the efficacy of the therapy provided by the stimulation system; that is, the more efficacious the therapy, the more diurnally active the patient will be. Thus, knowledge of the physical activity of the patient over a period of time in which therapeutic stimulation is applied to the patient may be used by a physician or clinician to prescribe pharmaceuticals, reprogram or upgrade the IPG, or implement or modify other therapeutic regimens (such as physical or occupational therapy). Knowledge of the physical activity of the patient may also be used to adapt the therapy provided by the stimulation system in real time, so that the stimulation is consistently provided to the patient at an efficacious and/or comfortable level. Further details discussing the tracking of the physical activity of a patient are provided in U.S. patent application Ser. No. 12/024,947, entitled "Neurostimulation System and Method for Measuring Patient Activity," which is expressly incorporated herein by reference.

There remains a need to provide improved techniques for characterizing the tissue surrounding a medical lead.

SUMMARY OF THE INVENTION

In accordance with the present inventions, a medical system configured for performing a medical function in a patient is provided. The medical system comprises at least one medical lead configured for being implanted adjacent a tissue region of the patient, and at least one sensing element. The sensing element(s) may be configured for being implanted adjacent the tissue region, and may comprise at least one electrode carried by the medical lead(s). The medical system further comprises monitoring circuitry configured for acquiring a plurality of physiological measurements from the sensing element(s) during one of a plurality of events (e.g., a plurality of postures or a plurality of subsets of postures) respectively corresponding to a plurality of classes. In one embodiment, a plurality of sensing elements are provided, in which case, the physiological measurements may respectively be acquired from the sensing elements. If the sensing element(s) are electrodes, the physiological measurements will be electrical measurements.

The medical system further comprises a processor configured for deriving a set of data from the plurality of physiological measurements. In one embodiment, the data set comprises one or both of electrical impedance values and field potential values. In another embodiment, the data set comprises different types of data (e.g., at least two of an impedance, field potential, evoked potential, pressure, tension, translucence, reflectance, pH, acceleration, chemical, respiration, vascular pulsation, heartbeat, ECG, EKG, and/or EMG, relative lead alignment, absolute lead movement, absolute lead position, and patient posture).

The processor is further configured for performing a feature extraction technique on the data set to acquire at least one feature (using one of a Principal Component Analysis, a Partial Least Square analysis, an Independent Component Analysis, and an artificial neural network), analyzing the feature(s), and classifying the data set into the one class corresponding to the one event. In one embodiment, each of the feature(s) has a coefficient, and the medical system further comprises memory storing at least one (n−1)-dimensional classification hyperplane that divides an n-dimensional space into a plurality of sub-spaces respectively corresponding to the plurality of different classes, wherein n equals the number of the feature(s). In this case, the processor is configured for classifying the data set into the one class by recalling the classification hyperplane from the memory, plotting the recalled classification hyperplane and a data point defined by the coefficient(s) in the n-dimensional space, and identifying the sub-space in which the data point is located.

The medical system further comprises a controller configured for performing a function based on the classified data set. The function may comprise identifying the one event (e.g., a posture and/or physical activity of the patient, a migration of the medical lead(s), or a stage of an encapsulation process with respect to the medical lead(s)) corresponding to the classified data set. The function may comprise a corrective action. For example, the medical system may comprise at least one electrode carried by the medical lead(s), and analog output circuitry configured for conveying therapeutic electrical energy to the electrode(s). The controller may be configured for programming the electrode(s) with a set of neurostimulation parameters prior to performing the function, in which case, the corrective action is modifying the neurostimulation parameter set and reprogramming the electrode(s) with the modified neurostimulation parameter set. As another example, the corrective action is providing a notification message or warning to a user.

The medical system may comprise an implantable casing containing the monitoring circuitry, the processor, and the controller. Or the medical system may comprise an external control device containing the processor and the controller.

In an optional embodiment, for each of the plurality of events, the monitoring circuitry is configured for acquiring at least one plurality of reference physiological measurements from the sensing element(s), in which case, the processor may be configured for deriving at least one set of reference data respectively from the plurality(ies) of reference physiological measurements, performing a feature extraction process on each of the reference data set(s) to acquire a set of reference features for the respective each reference data set, and defining the plurality of classes from the sets of reference features acquired over the plurality of events.

For example, of each set of reference features respectively has a set of coefficients, and the at least one plurality(ies) of reference physiological measurements for each event comprises at least two pluralities of reference physiological measurements, the processor may be configured for defining the plurality of classes by plotting a plurality of data points in an n-dimensional space, wherein n equals the number of the reference features in each set of reference features, and each of the data points is defined by the set of coefficients of the set of reference features. In this case, the processor may define the plurality of classes based on the plotted data points; for example by performing a pattern recognition technique (e.g., using one of machine learning, a classification algorithm, a clustering algorithm, a regression algorithm, and an artificial neural network) on the plotted data points. The processor may define the aforementioned classification hyperplane and store it in memory.

In the optional embodiment, the processor, for each of the plurality of events, may be configured for performing a feature selection technique on a plurality of reference features extracted from each of the reference data set(s), and performing a feature selection process (e.g., one of a clustering algorithm, inter-class distance based feature selection, intra-class based feature selection, probabilistic distance based feature selection, correlation based feature selection, consistency based feature selection, and entropy based feature selection) that identifies the most significant features that differ between the plurality of events. In this case, the acquired set of features includes only the most significant features.

In the optional embodiment, the medical system may further comprise at least one electrode carried by the medical lead(s), and telemetry circuitry configured for receiving different user-defined sets of stimulation parameters from an external control device. The different sets of stimulation parameters are respectively correlated to the plurality of events. The medical system further comprises analog output circuitry configured for conveying therapeutic electrical energy to the electrode(s) in accordance with the different user-defined sets of stimulation parameters. In this case, the monitoring circuitry is configured for acquiring the plurality (ies) of reference physiological measurements from the sensing element(s) in response to the receipt of each of the different user-defined sets of stimulation parameters from the external control device, and the function comprises instructing the analog output circuitry to convey the therapeutic electrical energy to electrode(s) in accordance with the set of stimulation parameters correlated to the one event.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a multi-lead system such as a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
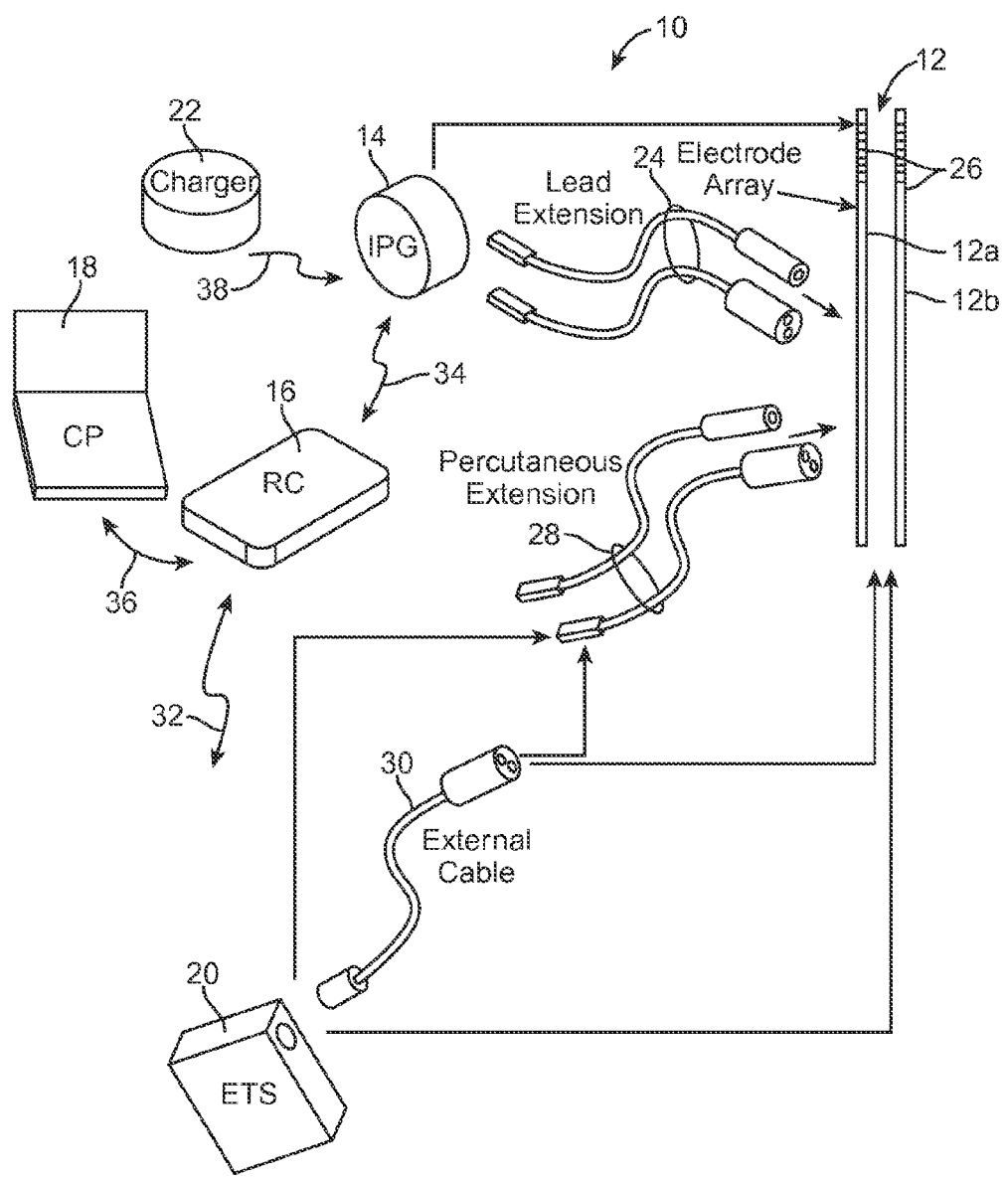
FIG. 1 is plan view of one embodiment of a spinal cord stimulation (SCS) system arranged in accordance with the present inventions.

Turning first to FIG. 1, an exemplary SCS system 10 generally comprises a plurality of neurostimulation leads 12 (in this case, two percutaneous leads 12a and 12b), an implantable pulse generator (IPG) 14, an external remote control (RC) 16, a Clinician's Programmer (CP) 18, an External Trial Stimulator (ETS) 20, and an external charger 22.

The IPG 14 is physically connected via two lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neuromodulation leads 12. The number of neuromodulation leads 12 illustrated is two, although any suitable number of neuromodulation leads 12 can be provided, including only one. Alternatively, a surgical paddle lead can be used in place of one or more of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters. The IPG 14 and neurostimulation leads 12 can be provided as an implantable neurostimulation kit, along with, e.g., a hollow needle, a stylet, a tunneling tool, and a tunneling straw. Further details discussing implantable kits are disclosed in U.S. Application Ser. No. 61/030,506, entitled "Temporary Neurostimulation Lead Identification Device," which is expressly incorporated herein by reference.

The ETS 20 may also be physically connected via percutaneous lead extensions 28 or external cable 30 to the neurostimulation lead 12. The ETS 20, which has similar pulse generation circuitry as the IPG 14, also delivers electrical stimulation energy in the form of an pulsed electrical waveform to the electrode array 26 in accordance with a set of stimulation parameters. The major difference between the ETS 20 and the IPG 14 is that the ETS 20 is a non-implantable device that is used on a trial basis after the neurostimulation lead 12 has been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For the purposes of this specification, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuroplasticity or neurogenesis of brain tissue. For purposes of brevity, the details of the CP 18, ETS 20, and external charger 22 will not be described herein. Details of exemplary embodiments of these components are disclosed in U.S. Pat. No. 6,895,280, which is expressly incorporated herein by reference.

Figure 2:
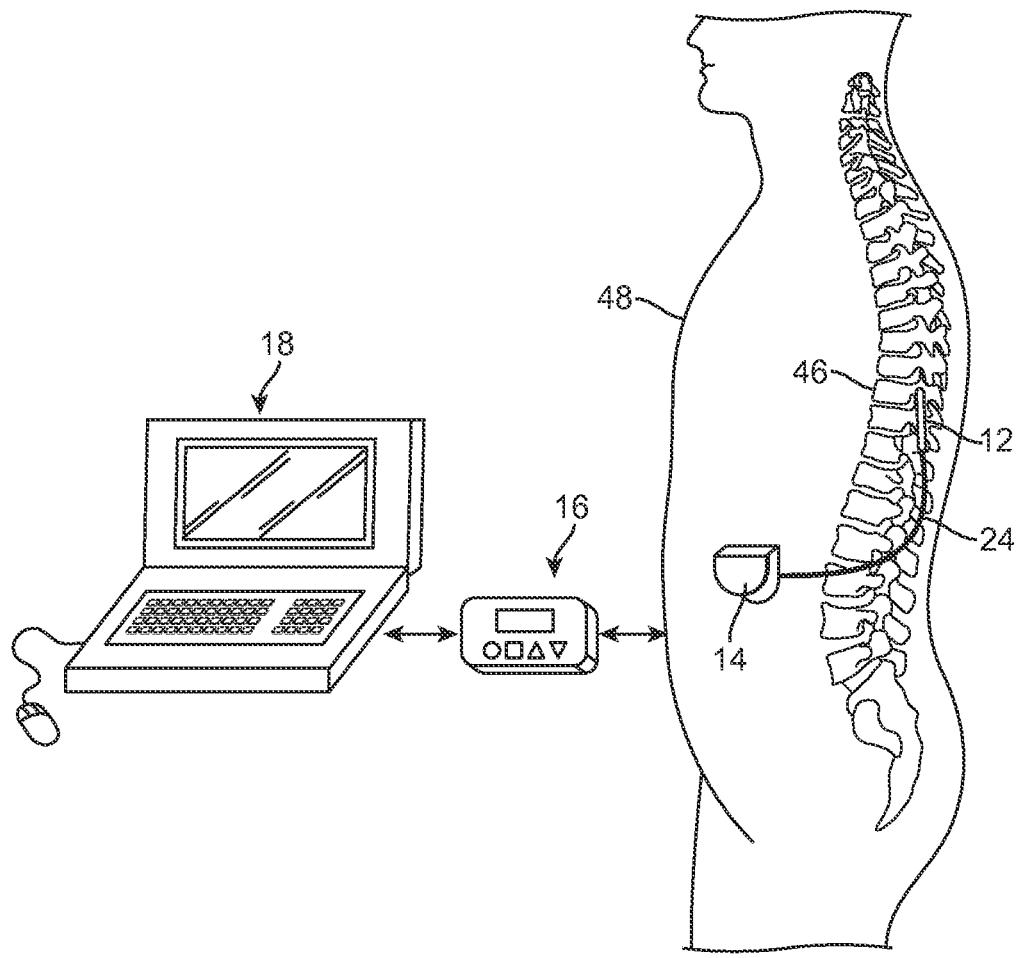
FIG. 2 is a plan view of the SCS system of FIG. 1 in use with a patient.

Referring to FIG. 2, the neurostimulation leads 12 are implanted at an initial position within the spinal column 46 of a patient 48. The preferred placement of the neurostimulation leads 12 is adjacent, i.e., resting near, or upon the dura, adjacent to the spinal cord area to be stimulated. Due to the lack of space near the location where the neurostimulation leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the neurostimulation leads 12. As there shown, the CP 18 communicates with the IPG 14 via the RC 16. After implantation, the IPG 14 can be operated to generate a volume of activation relative to the target tissue to be treated, thereby providing the therapeutic stimulation under control of the patient.

Figure 3:
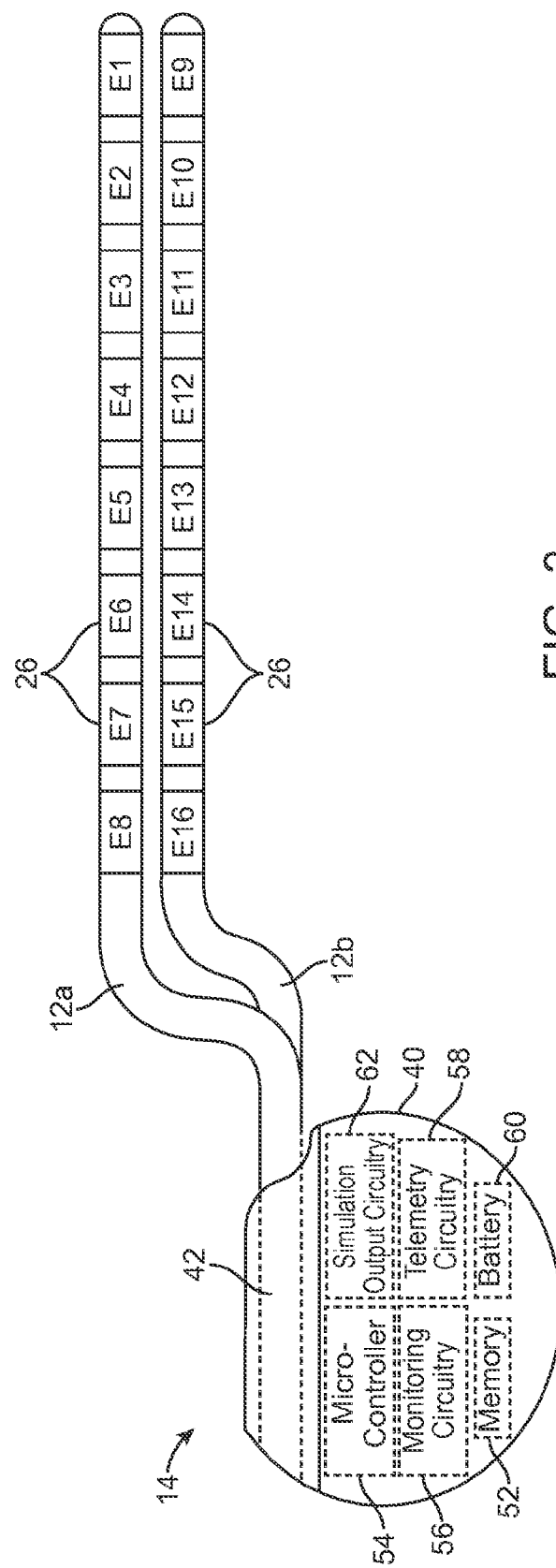
FIG. 3 is a plan view of an implantable pulse generator (IPG) and two neurostimulation leads used in the SCS system of FIG. 1.

Referring now to FIG. 3, the external features of the neurostimulation leads 12a, 12b and the IPG 14 will be briefly described. Each of the neurostimulation leads 12 has eight electrodes 26 (respectively labeled E1-E8 for the lead 12a and E9-E16 for the lead 12b). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IPG 14 comprises an outer case 40 for housing the electronic and other components (described in further detail below). The outer case 40 is composed of an electrically conductive, biocompatible material, such as titanium, and forms a hermetically sealed compartment wherein the internal electronics are protected from the body tissue and fluids. In some cases, the outer case 40 may serve as an electrode. The IPG 14 further comprises a connector 42 to which the proximal ends of the neurostimulation leads 12 mate in a manner that electrically couples the electrodes 26 to the internal electronics (described in further detail below) within the outer case 40. To this end, the connector 42 includes two ports (not shown) for receiving the proximal ends of the leads 12. In the case where the lead extensions 24 are used, the ports may instead receive the proximal ends of such lead extensions 24.

As briefly discussed above, the IPG 14 includes circuitry that provides electrical stimulation energy to the electrodes 26 in accordance with a set of parameters. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y). As will be described in further detail below, the IPG 14 also includes circuitry that provides electrical signals, and measured electrical impedance in response to the electrical signals.

With respect to the pulsed electrical waveform provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 40, so that the electrical current has a path from the energy source contained within the IPG case 40 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 40 of the IPG 14, so that electrical energy is transmitted between the selected electrode 26 and case 40. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

The IPG 14 comprises electronic components, such as a memory 52, controller/processor (e.g., a microcontroller) 54, monitoring circuitry 56, telemetry circuitry 58, a battery 60, stimulation output circuitry 62, and other suitable components known to those skilled in the art.

The memory 52 is configured for storing programming packages, stimulation parameters, measured physiological information, and other important information necessary for proper functioning of the IPG 14. The microcontroller 54 executes a suitable program stored in memory 52 for directing and controlling the neurostimulation performed by IPG 14. The monitoring circuitry 56 is configured for monitoring the status of various nodes or other points throughout the IPG 14, e.g., power supply voltages, temperature, battery voltage, and the like. Notably, the electrodes 26 fit snugly within the epidural space of the spinal column 46, and because the tissue is conductive, electrical measurements can be taken between the electrodes 26. Thus, the monitoring circuitry 56 is configured for taking such electrical measurements (e.g., electrode impedance, field potential, evoked action potentials, etc.) for performing such functions as detecting fault conditions between the electrodes 26 and the stimulation output circuitry 62, determining the coupling efficiency between the electrodes 26 and the tissue, determining the posture/patient activity of the patient, facilitating lead migration detection, etc.

Electrical signals can be transmitted between electrodes 26 carried by one of the neurostimulation leads 12 and one or more other electrodes (e.g., electrodes on the same neurostimulation lead 12, electrodes on the other neurostimulation lead 12, the case 40 of the IPG 12, or an electrode affixed to the tissue), and then electrical parameters can be measured in response to the transmission of the electrical signals.

Electrical data can be measured using any one of a variety means. For example, the electrical data measurements can be made on a sampled basis during a portion of the time while the electrical stimulus pulse is being applied to the tissue, or immediately subsequent to stimulation, as described in U.S. patent application Ser. No. 10/364,436, which has previously been incorporated herein by reference. Alternatively, the electrical data measurements can be made independently of the electrical stimulation pulses, such as described in U.S. Pat. Nos. 6,516,227 and 6,993,384, which are expressly incorporated herein by reference. For example, electrical data measurements can be made in response to alternating current (AC) or pulsatile electrical signals, which preferably use amplitudes and pulsewidths (e.g., 1 mA for 20 µs) that generate no physiological response for the patient (i.e., subthreshold), but can alternatively be performed in response to stimulation pulses.

The impedance measurement technique may be performed by applying a known current between a pair of electrodes 26, a voltage between the electrodes 26 can be measured, and an impedance between the electrodes 26 can be calculated as a ratio of the measured voltage to known current. Or a known voltage can be applied between a pair of electrodes 26, a current between the electrodes 26 can be measured, and an impedance between the electrodes 26 can be calculated as a ratio of the known voltage to measured current.

The field potential measurement technique may be performed by generating an electrical field at selected ones of the electrodes 26 using constant current and recording the electrical field at other selected ones of the lead electrodes 26. This may be accomplished in one of a variety of manners. For example, an electrical field may be generated by conveying electrical energy to a selected one of the electrodes 26 and returning the electrical energy at the IPG case 40. Alternatively, multipolar configurations (e.g., bipolar or tripolar) may be created between the lead electrodes 26. Or, an electrode that is sutured (or otherwise permanently or temporarily attached (e.g., an adhesive or gel-based electrode) anywhere on the patient's body may be used in place of the case IPG outer case or lead electrodes 26. In either case, while a selected one of the electrodes 26 is activated to generate the electrical field, a selected one of the electrodes 26 (which may include the activated electrode or another electrode) is operated to record the voltage potential of the electrical field. Alternatively, a differential field potential measurement between a pair of electrodes that are different from the electrodes that source and return the energy can be taken.

The evoked potential measurement technique may be performed by generating an electrical field at one of the electrodes 26, which is strong enough to depolarize the neurons adjacent the stimulating electrode beyond a threshold level, thereby inducing the firing of action potentials (APs) that propagate along the neural fibers. Such stimulation is preferably supra-threshold, but not uncomfortable. A suitable stimulation pulse for this purpose is, for example, 4 mA for 200 µs. While a selected one of the electrodes 26 is activated to generate the electrical field, a selected one or ones of the electrodes 26 (different from the activated electrode) is operated to record a measurable deviation in the voltage caused by the evoked potential due to the stimulation pulse at the stimulating electrode.

Further details discussing the measurement of electrical parameter data, such as electrode impedance, field potential, and evoked action potentials are set forth in U.S. patent application Ser. No. 10/364,436, entitled "Neural Stimulation System Providing Auto Adjustment of Stimulus Output as a Function of Sensed Impedance," U.S. patent application Ser. No. 10/364,434, entitled "Neural Stimulation System Providing Auto Adjustment of Stimulus Output as a Function of Sensed Pressure Changes," U.S. Pat. No. 6,993,384, entitled "Apparatus and Method for Determining the Relative Position and Orientation of Stimulation Leads," and U.S. patent application Ser. No. 11/096,483, entitled "Apparatus and Methods for Detecting Migration of Stimulation Leads," which are expressly incorporated herein by reference.

It should be noted that the monitoring circuitry 56 may acquire physiological measurements other than impedance, field potential, and evoked action potential measurements. For example, using a separate sensor (not shown), the monitoring circuitry 56 may acquire pressure, tension, translucence, reflectance, pH, acceleration, chemical, respiration, vascular pulsation, heartbeat, ECG, EKG, and/or EMG.

The telemetry circuitry 58, including an antenna (not shown), is configured for receiving programming data (e.g., the operating program and/or stimulation parameters) from the RC 16 and/or CP 18 in an appropriate modulated carrier signal, which the programming data is then stored in the memory 52. The telemetry circuitry 58 is also configured for transmitting status data to the RC 16 and/or CP 18 in an appropriate modulated carrier signal. The battery 60, which may be a rechargeable lithium-ion or lithium-ion polymer battery, provides operating power to IPG 14. The stimulation output circuitry 62 is configured for, under control of the microcontroller 54, generating and delivering electrical energy, in the form of electrical pulse trains, to each of the electrodes 26, as well as any electrical signals needed for acquiring electrical measurements.

Notably, while the controller/processor 54 is shown in FIG. 3 as a single device, the processing functions and controlling functions can be performed by a separate controller and processor. Thus, it can be appreciated that the controlling functions performed by the IPG 14 can be performed by a controller, and the processing functions performed by the IPG 14 can be performed by a processor. Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-modulator (not shown) connected to the leads 12. In this case, the power source, e.g., a battery, for powering the implanted receiver, as well as control circuitry to command the receiver-modulator, will be contained in an external controller inductively coupled to the receiver-modulator via an electromagnetic link. Data/power signals are transcutaneously coupled from a cable-connected transmission coil placed over the implanted receiver-modulator. The implanted receiver-modulator receives the signal and generates the modulation in accordance with the control signals.

Figure 4:
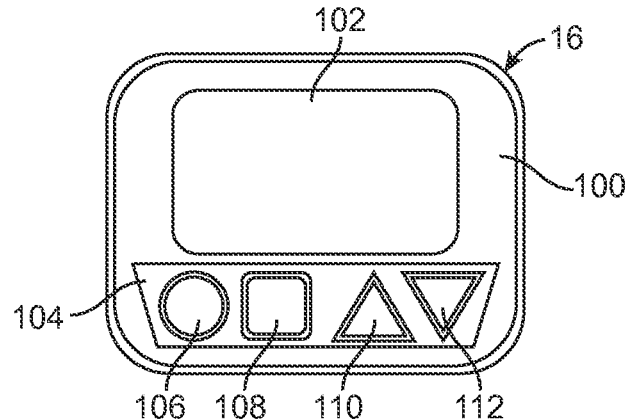
FIG. 4 is a plan view of a remote control that can be used in the SCS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), a lighted display screen 102, an audio transducer (speaker) 103, and a control pad 104 carried by the exterior of the casing 100. In the illustrated embodiment, the display screen 102 is a lighted flat panel display screen, and the control pad 104 comprises a membrane switch with metal domes positioned over a flex circuit, and a keypad connector connected directly to a PCB. In an optional embodiment, the display screen 102 has touchscreen capabilities. The control pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 16 to switch between screen displays and/or parameters. The buttons 110 and 112 serve as up/down buttons that can be actuated to increase or decrease any of stimulation parameters of the pulse generated by the IPG 14, including pulse amplitude, pulse width, and pulse rate.

Figure 5:
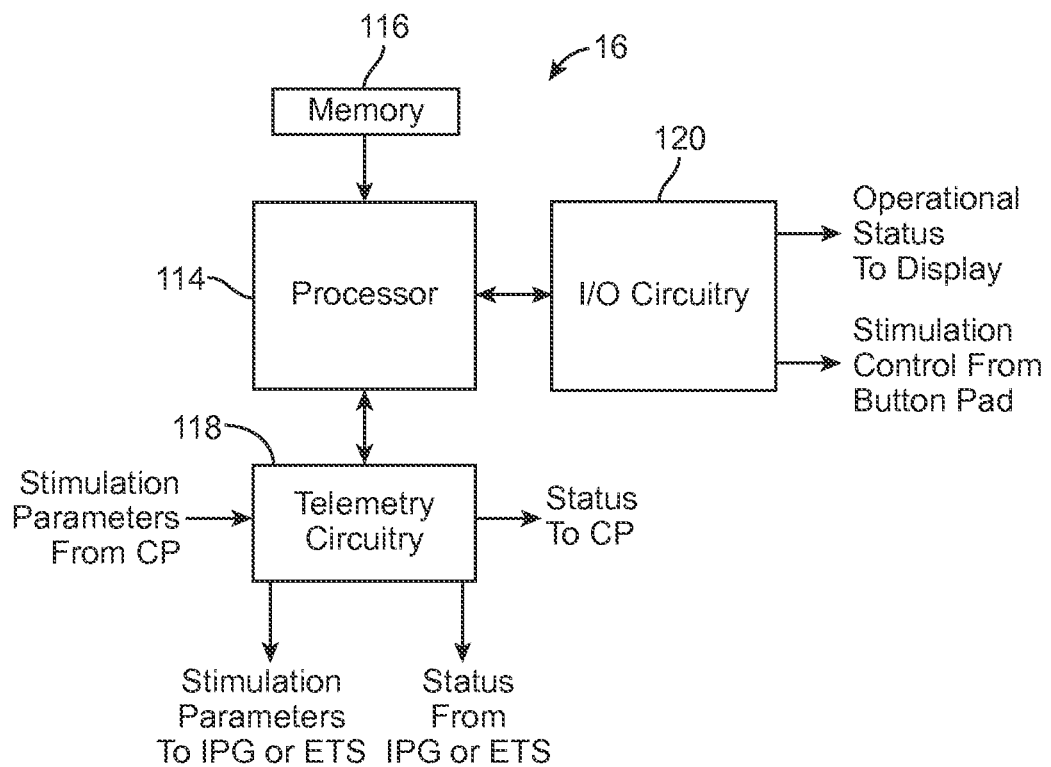
FIG. 5 is a block diagram of the internal componentry of the remote control of FIG. 4.

Referring to FIG. 5, the internal components of an exemplary RC 16 will now be described. The RC 16 generally includes a controller/processor 114 (e.g., a microcontroller), memory 116 that stores an operating program for execution by the controller/processor 114, and telemetry circuitry 118 for transmitting control data (including stimulation parameters and requests to provide status information) to the IPG 14 and receiving status information (including the measured electrical data) from the IPG 14 via link 34 (or link 32) (shown in FIG. 1), as well as receiving the control data from the CP 18 and transmitting the status data to the CP 18 via link 36 (shown in FIG. 1). The RC 16 further includes input/output circuitry 120 for receiving stimulation control signals from the control pad 104 and transmitting operational status information to the display screen 102 and speaker 103 (shown in FIG. 4). Notably, while the controller/processor 114 is shown in FIG. 5 as a single device, the processing functions and controlling functions can be performed by a separate controller and processor. Thus, it can be appreciated that the controlling functions performed by the RC 16 can be performed by a controller, and the processing functions performed by the RC 16 can be performed by a processor. Further details of the functionality and internal componentry of the RC 16 are disclosed in U.S. Pat. No. 6,895,280, which has previously been incorporated herein by reference.

As previously mentioned in the background of the invention, the tissue environment in which the neurostimulation leads 12 may change due to lead migration (either relative to each other or relative to a point in reference point in the tissue), tissue encapsulation, posture changes, patient activity, etc. The SCS system 10 is capable of compensating for these environmental changes between the neurostimulation leads 12 and tissue.

To the end, the SCS system 10 is configured for acquiring a plurality of physiological measurements from the patient. As previously discussed, these physiological measurements can be acquired by the monitoring circuitry 56 of the IPG 14, although it should be appreciated that monitoring circuitry separate from the IPG 14 may be alternatively acquire some or all of the physiological measurements. As also previously discussed, the physiological measurements may be electrical measurements taken by the electrodes 26 or may be electrical measurements or non-electrical measurements taken by separate sensors, which may be implanted adjacent the neurostimulation leads 12 or may be located in or on the patient remote from the neurostimulation leads 12.

In any event, the physiological measurements are acquired during one of a plurality of events. As one example, each event may be a posture and/or patient activity (e.g., supine, prone, sit, standing up, and walking) or a group of postures (e.g., supine and prone versus sit, standing up, and walking). As another example, each event may be a different migration of the neurostimulation leads 12 relative to each other or relative to the tissue. As still another example, each event may be a different stage in an encapsulation process.

The SCS system 10 is capable of efficiently processing the physiological measurements that compensates for any changes in the tissue environment relative to the neurostimulation leads 12. In the preferred embodiment, the microcontroller 54 of the IPG 14 processes the physiological measurements, although it should be appreciated that controller/processor circuitry separate from the IPG 14, e.g., microcontroller 114 of the RC 16, may process the physiological measurements. In the latter case, the physiological measurements may be telemetered from the IPG 14 to the RC 16 for processing by the RC 16. However, it should be appreciated that it is particularly advantageous that the microcontroller 54 of the IPG 14 process the physiological measurements, which would obviate the need for communication between the IPG 14 and the RC 16 during processing of the physiological measurements.

To this end, the SCS system 10 is configured for deriving a set of data from the physiological measurements. This data set can be derived directly from the values of the physiological measurements (i.e., the values of the data set are the values of the physiological measurements) or can be derived indirectly from the values of the physiological measurements.

The indirectly derived data may include, e.g., relative lead position or migration, absolute lead position or movement (relative to tissue), patient posture, etc. Rostro-caudal migration (lead stagger) can be determined in accordance with the techniques disclosed in U.S. Pat. No. 6,993,384, entitled "Apparatus and Method for Determining the Relative Position and Orientation of Neurostimulation Leads," U.S. Pat. No. 7,831,307, entitled "System and Method for Computationally Determining Migration of Neurostimulation Leads," and U.S. patent application Ser. No. 12/550,136, entitled "Method and Apparatus for Determining Relative Positioning Between Neurostimulation Leads," which are expressly incorporated herein by reference. Medio-lateral migration (lateral lead separation) can be determined in accordance with the technique disclosed in U.S. patent application Ser. No. 12/623,976, entitled "Method and Apparatus for Determining Relative Positioning Between Neurostimulation Leads," which is expressly incorporated herein by reference. Relevant dorsal-ventral migration (lead depth), as well as the absolute lead migration can be determined in accordance with the techniques disclosed in U.S. patent application Ser. No. 11/096,483, entitled "Apparatus and Methods for Detecting Migration of Neurostimulation Leads," and U.S. patent application Ser. No. 12/495,442, entitled "System and Method for Compensating for Shifting of Neurostimulation Leads in a Patient," which are expressly incorporated herein by reference. Optical interferometer techniques or ultrasound distance measuring techniques can alternatively be used to measure the relative dorsal-ventral lead migration. The posture or postural changes in the patient can be determined in accordance with the techniques described in U.S. patent application Ser. No.

13/446,191, entitled "Sensing Device Indicating Posture of Patient Implanted with a Neurostimulation Device," U.S. Pat. No. 7,317,948, entitled "Neural Stimulation System Providing Auto Adjustment of Stimulus Output as Function of Sensed Impedance," which are expressly incorporated herein by reference.

Indirectly derived data may also include monopolar or bipolar field potentials that are derived from impedance measurements, or monopolar or bipolar impedances derived from field potential measurements, as discussed in the techniques set forth in U.S. patent application Ser. No. 12/856,905, entitled "Apparatus and Method for Determining the Relative Position and Orientation of Neurostimulation Leads," which is expressly incorporated herein by reference.

The SCS system 10 is further configured for performing a feature extraction technique on the data set to acquire at least one feature. Significantly, a feature extraction technique transforms a set of input data into a reduced representation set of features that are carefully chosen to extract the relevant information from the input data in order to perform the desired task using this reduced representation instead of all of the input data. Analysis with a large number of variables, and in this case the data, generally requires a large amount of memory and computation power or a classification algorithm, which overfits the training sample and generalizes poorly to new samples. Feature extraction is a general term for methods of constructing combinations of the variables to get around these problems while still describing the data with sufficient accuracy. The feature extraction technique may be performed, e.g., using one of a Principal Component Analysis, a Partial Least Square analysis, an Independent Component Analysis, and an artificial neural network.

The SCS system 10 is further configured for analyzing the feature(s) and classifying the data set into one of a plurality of classes respectively corresponding the plurality of events. In one embodiment, the SCS system 10 stores at least one (n−1)-dimensional classification hyperplane that divides an n-dimensional space into a plurality of sub-spaces respectively corresponding to the plurality of different events, wherein n equals the number of feature(s). In the preferred embodiment, the memory 52 of the IPG 14 stores the classification hyperplane. Of course, if the microcontroller 114 of the RC 16 processes the physiological measurements, it may be more convenient for the memory 116 of the RC 16 to store the classification hyperplane.

Figure 6:
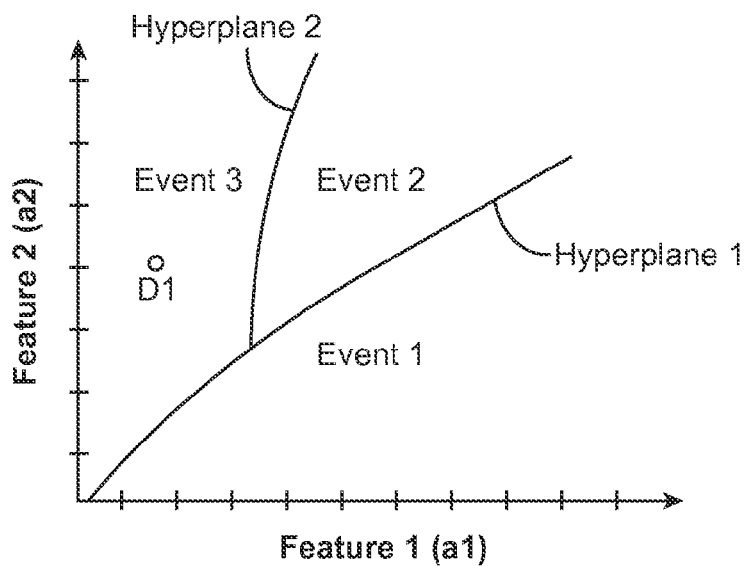
FIG. 6 is a diagram illustrating a data point extracted from physiological measurements and plotted by the SCS system of FIG. 1 in a two-dimensional space divided by two one-dimensional classification hyperplanes into three sub-spaces respectively corresponding to three events.
Figure 7:
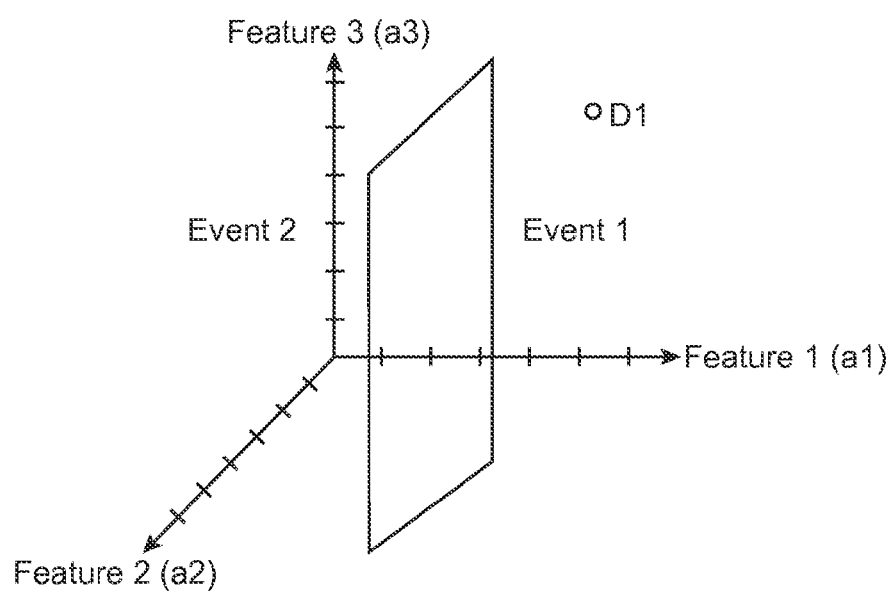
FIG. 7 is a diagram illustrating a data point extracted from physiological measurements and plotted by the SCS system of FIG. 1 in a three-dimensional space divided by a two-dimensional classification hyperplane into two sub-spaces respectively corresponding to two events.

For the purposes of this specification, a "classification hyperplane" is a sub-space having one less dimension than the ambient space. Therefore, if the ambient space is three-dimensional, the classification hyperplane is two-dimensional. If the ambient space is two-dimensional, the classification hyperplane is one-dimensional. For example, as illustrated in FIG. 6, two one-dimensional classification hyperplanes divide a two-dimensional space (two features) into three sub-spaces corresponding to Events E1-E3. As illustrated in FIG. 7, a two-dimensional classification hyperplane divides a three-dimensional space (three features) into two sub-spaces corresponding to Events E1-E2. Of course, the ambient space can be less than two dimensions or greater than three dimensions, and will ultimately depend on the number of features extracted from the data set.

Each of the feature(s) has a coefficient (i.e., the number or constant that multiplies the feature or variable). For example, the extracted data can be expressed as $a_1F_1+a_2F_2+a_3F_3\ldots$, where a is the coefficient, and F is the feature. The SCS system 10 is configured for classifying the data set into the class corresponding to the one event by recalling the stored classification hyperplane, optionally plotting a data point defined by the coefficient(s) and the classification hyperplane in the n-dimensional space, and identifying the sub-space in which the data point is located. For example, as illustrated in FIG. 6, the data point D1 defined by coefficients $a_1$ and $a_2$ is plotted in the two-dimensional space within the sub-space corresponding with event E3. As illustrated in FIG. 7, the data point D1 defined by coefficients $a_1$-$a_3$ is plotted in the three-dimensional space within the sub-space corresponding with event E1.

The SCS system 10 is lastly configured for performing a function based on the classified data set. In one embodiment, the function that is performed is identifying the one event corresponding to the classified data set, and in the illustrated embodiment, the sub-space in which the data point D1 is located. For example, although not required, the SCS system 10 may correlate the actual events to the sub-spaces, as further detail described below, and once the sub-space in which the data point D1 is located is identified, the event corresponding to the identified sub-space may be identified. In another embodiment, the performance of the function is a corrective action; for example, reprogramming the IPG 14 with a modified set of stimulation parameters and/or providing a user-discernible message (e.g., an alert or warning).

In the latter case, the user-discernible message may take the form of an aural signal (e.g., distinctive tones, patterns of sounds, music, voice messages, etc.) conveyed to the user via the speaker 103 of the RC 16, a visual signal (e.g., a blinking icon) conveyed to the user via the display 102 of the RC 16, a vibratory signal conveyed to the user via the case 100 of the RC 16, or a modulated neurostimulation signal (e.g., pulsing a neurostimulation signal on and off at a frequency less than the pulse frequency (e.g., every three seconds) or repeatedly increasing and decreasing the amplitude of the neurostimulation signal) that can be perceived by the patient as distinguished from normal, operative stimulation used for the therapy. The corrective action may be taken by the microcontroller 54 of the IPG 14, which may be advantageous to obviate the need to communicate with the RC 16. However, if the user-discernible message is conveyed via the RC 16, it may be advantageous for the microcontroller 114 of the RC 16 may take the corrective action.

Figure 8:
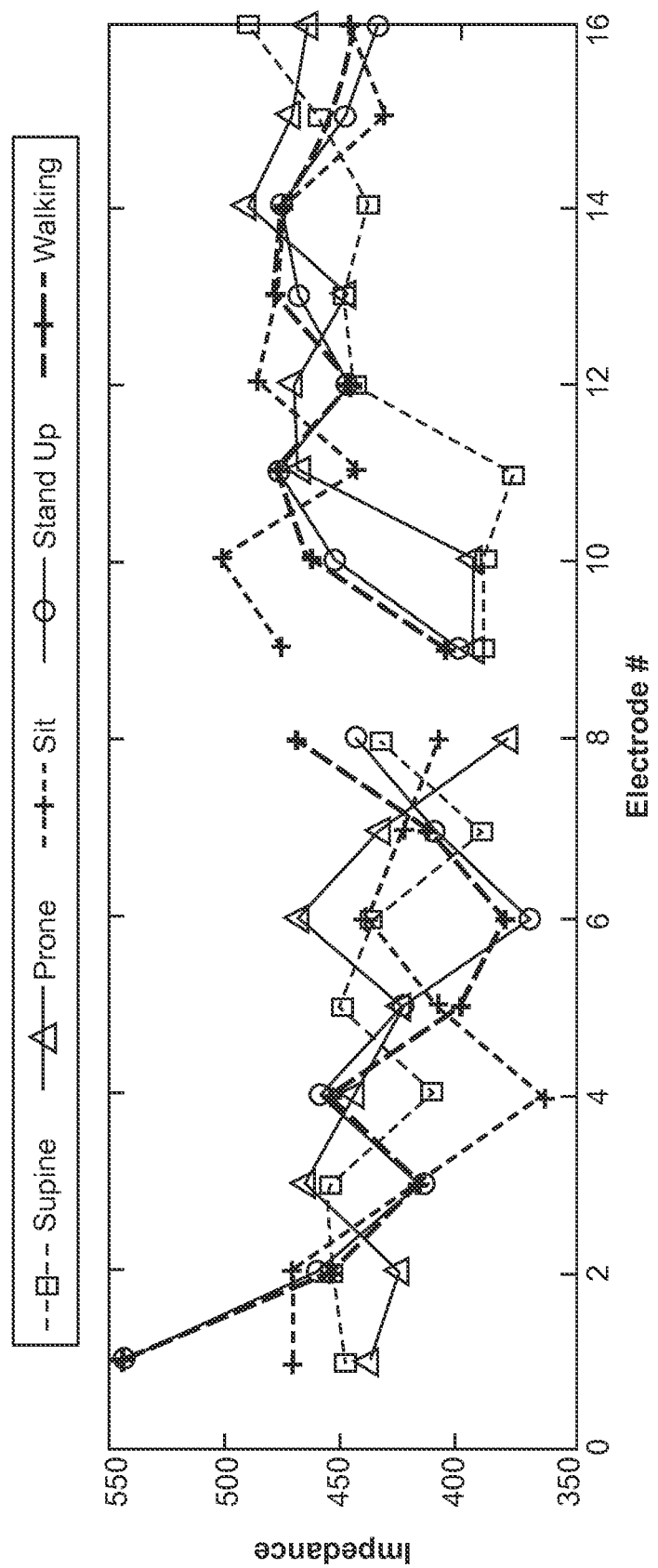
FIG. 8 is a diagram illustrating impedance measurements taken by the SCS system of FIG. 1 at sixteen electrodes taken across five different postures.

The SCS system 10 may be configured for being trained to accurately correlate the physiological measurements with different events. In particular, the SCS system 10, for each of the events, may acquire one or more pluralities of reference physiological measurements, and derive at least one set of reference data respectively from the plurality(ies) of reference physiological measurements. In one example, the SCS system 10 acquires reference impedance measurements respectively at the sixteen electrodes during each of five different postures (supine, prone, sit, stand up, and walking), as illustrated in FIG. 8. The reference impedance measurements for each of the five different postures may be repeated a multitude of times to produce multiple sets of reference data for each posture. For example, the patient may cycle through all of the postures in different orders and at vastly different times (e.g., a week apart between cycles) to produce six sets of reference data for each posture for a total of thirty sets of reference data for all five postures.

The SCS system 10 may then perform a feature extraction process on each set of reference data to acquire a set of reference features for that set of reference data. Thus, for six sets of reference data for each posture, there will be six sets of reference features for that posture for a total of thirty sets of reference features for all five features. The SCS system 10 may then define a plurality of classes from the sets of reference features acquired over the plurality of events. In one embodiment, each set of reference features respectively has a set of coefficients, and several pluralities of physiological measurements are acquired for each event (e.g., six sets of physiological measurements for each posture, in the example discussed above).

Figure 9:
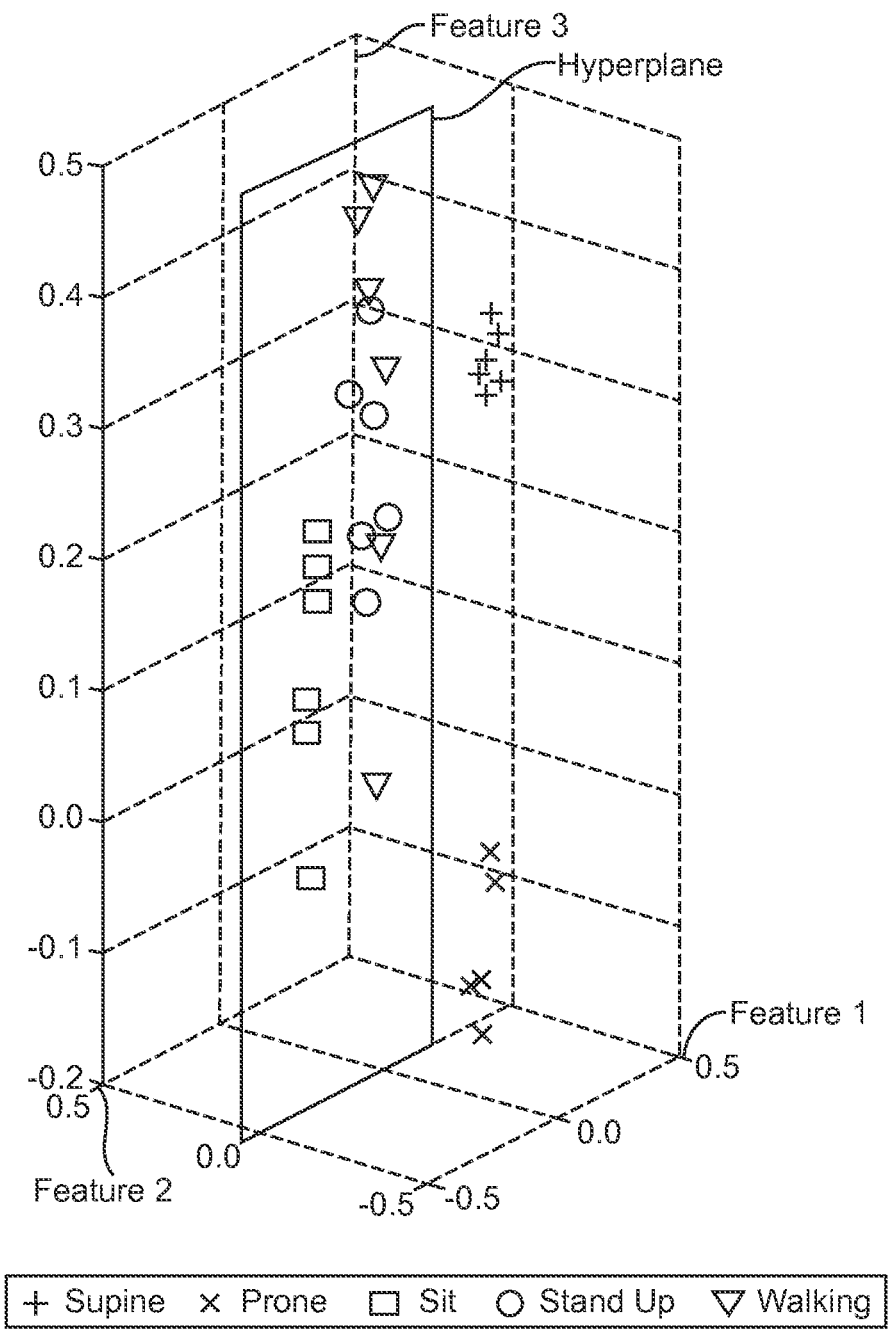
FIG. 9 is a diagram illustrating data points extracted from repeated impedance measurements over five different postures and plotted by the SCS system of FIG. 1 in a three-dimensional space divided by a two-dimensional classification hyperplane into two sub-spaces respectively corresponding to two classes.

The SCS system 10 then plots a plurality of data points, each of which is defined by the set of coefficients of the respective set of reference features, in the n-dimensional space. For example, in the illustrated example, six data points will be defined for each posture (corresponding to the six sets of physiological measurements for each posture). Assuming a set of three reference features will be extracted from each set of reference data and the data will be represented with an equal number of three coefficients, the data points will be plotted in a three-dimensional space, as illustrated in FIG. 9.

The SCS system 10 then defines a plurality of classes based on the plotted data points by defining at least one (n−1)-dimensional classification hyperplane that divides the n-dimensional space into a plurality of sub-spaces respectively corresponding to the plurality of classes. In the example illustrated in FIG. 9, a two-dimensional classification hyperplane that divides the three-dimensional space into two sub-spaces respectively corresponding to two classes is defined, with the first class including the data points corresponding to the supine and prone postures, and the second class including the data points corresponding to the sit, stand up and walking postures. In effect, the five specific postures have been reduced down to two events (one event including the supine and prone postures, and another event including the sit, stand up and walking postures).

In the above case, the classification is binary (two classes). In the case where more than two classes exist, the classification can be cascaded, meaning that multiple binary classifications may be performed in sequence. For example, the classification technique may first classify between supine/prone versus sit/stand/walking as a binary classification; next, for those classified into the supine/prone group, perform another binary classification to classify between supine versus prone; next for those classified into the sit/stand/walking group, perform another binary classification to classify between two of the sit/stand/walking and the remaining one of the sit/stand/walking, and so forth. Alternatively, the classification can be a majority voting classification, where binary classification is performed between each pair of classes, and a sample is designated to the class that has been mostly classified into.

A classifier may be defined, e.g., using a manual technique or automatically with a pattern recognition technique, such as one of machine learning, a classification algorithm, a clustering algorithm, a nearest neighbor algorithm, a regression algorithm, and an artificial neural network. In the case of machine learning or an artificial neural network, the classifier may be a classification hyperplane. In the case of a clustering algorithm or a regression algorithm, the classifier may be a probability or a metric that indicates the class assignment. This classifier can then be stored for subsequent recall in classifying data as described above.

In one embodiment, a feature selection technique (e.g. a clustering algorithm, inter-class distance based feature extraction, intra-class based feature extraction, probabilistic distance based feature extraction, correlation based feature extraction, consistency based feature extraction, and entropy based feature extraction), is performed on an initial plurality of features extracted from each set of reference data that identifies the most significant features that differ between the plurality of events. Only the most significant features are then used as the acquired set of features.

Figure 10:
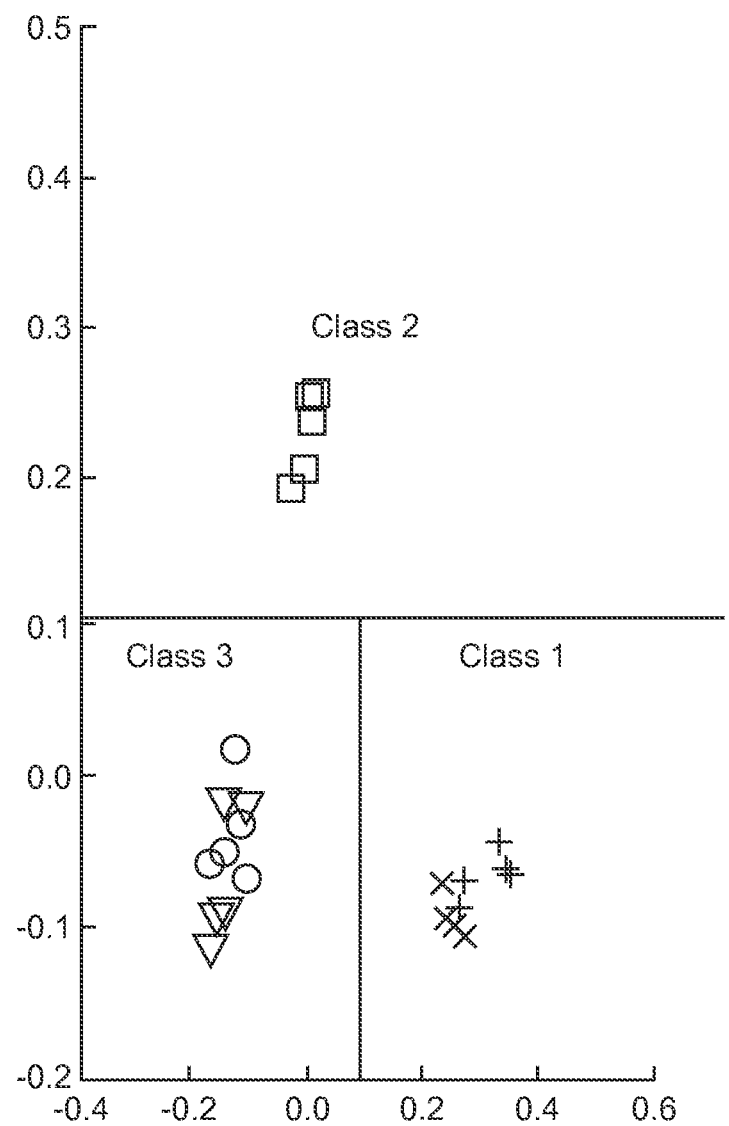
FIG. 10 is a diagram illustrating data points extracted from repeated impedance measurements over five different postures and plotted by the SCS system of FIG. 1 in a two-dimensional space divided by two one-dimensional classification hyperplanes into three sub-spaces respectively corresponding to three classes.

For example, one of the features extracted from the sets of reference data described above can be eliminated, such that two features for each set of reference data is used. In this case, the data points will be plotted in a two-dimensional space, as illustrated in FIG. 10. Two one-dimensional classification hyperplane (i.e., lines) that divides the two-dimensional space into three sub-spaces respectively corresponding to three classes is defined, with the first class including the data points corresponding to the supine and prone postures, the second class including the data points corresponding to the sit posture, and the third class including the data points corresponding to the stand up and walking postures. In effect, the five specific postures have been reduced down to three events (one event including the supine and prone postures, another event including the sitting posture, and still another event including the stand up and walking postures).

Although the example shown in FIGS. 8-10 utilizes only impedance measurements as the reference physiological measurements, it should be appreciated that different types of physiological measurements can be acquired in a training regimen to accurately correlate the physiological measurements to the events. For example, the reference physiological measurements may consist of monopolar impedance measurements, bipolar impedance measurements (between both adjacent electrodes and non-adjacent electrodes), differential field potential between adjacent electrodes, and lead stagger. In the same manner discussed above, the reference physiological measurements for each of the five different postures may be repeated a multitude of times to produce multiple sets of reference data for each posture. For example, the patient may cycle through all of the postures in different orders and at vastly different times (e.g., a week apart between cycles) to produce twelve sets of reference data for each posture for a total of sixty sets of reference data for all five postures.

Figure 11:
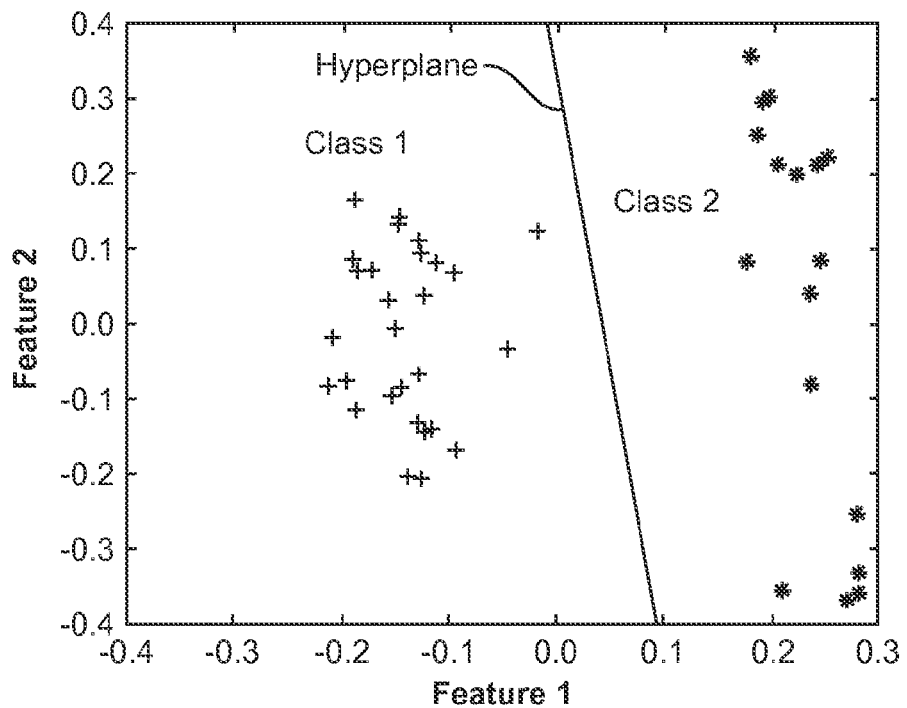
FIG. 11 is a diagram illustrating data points extracted from repeated various types of physiological measurements over five different postures and plotted by the SCS system of FIG. 1 in a two-dimensional space divided by a one-dimensional rectilinear classification hyperplane into two sub-spaces respectively corresponding to two classes.

The SCS system 10 then plots a plurality of data points, each of which is defined by the set of coefficients of the respective set of reference features, in the n-dimensional space. For example, in the illustrated example, twelve data points will be defined for each posture (corresponding to the twelve sets of physiological measurements for each posture). Assuming a set of two reference features will be extracted from each set of reference data and an equal number of two coefficients, the data points will be plotted in a two-dimensional space, as illustrated in FIG. 11.

Figure 12:
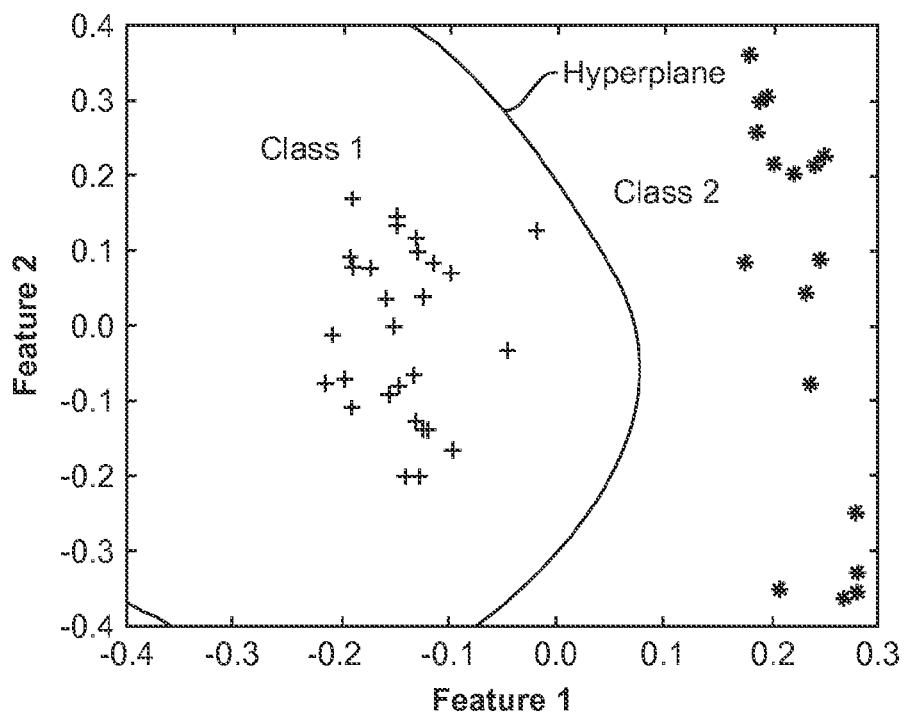
FIG. 12 is a diagram illustrating data points extracted from repeated various types of physiological measurements over five different postures and plotted by the SCS system of FIG. 1 in a two-dimensional space divided by a one-dimensional curvilinear classification hyperplane into two sub-spaces respectively corresponding to two classes.

The SCS system 10 then defines a plurality of classes based on the plotted data points by defining at least one (n−1)-dimensional classification hyperplane that divides the n-dimensional space into a plurality of sub-spaces respectively corresponding to the plurality of classes. In the example illustrated in FIG. 11, a one-dimensional classification hyperplane that divides the two-dimensional space into two sub-spaces respectively corresponding to two classes is defined, with the first class including the data points corresponding to the supine and prone postures, and the second class including the data points corresponding to the sit, stand up and walking postures. As shown in FIG. 11, the classification hyperplane is rectilinear, although as illustrated in FIG. 12, the classification hyperplane may be curvilinear to better define the classes.

In an optional embodiment, the SCM system 10 tracks and records stimulation program set up and patient operations, such that the classified events can be correlated with the stimulation settings and/or patient operation, thereby allowing for dynamic adaptive adjustment of the stimulation settings based on the classified events. To this end, the SCM system 10 is configured for acquiring the plurality(ies) of physiological measurements in response to the receipt of each of different user-defined sets of stimulation parameters from the RC 16. In this case, the function performed by the SCM system 10 comprises conveying the therapeutic electrical energy to the electrodes 26 in accordance with the set of stimulation parameters correlated to the one event.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A medical system configured for performing a medical function in a patient, comprising:
   at least one medical lead configured for being implanted adjacent a tissue region of the patient;
   at least one sensing element;
   monitoring circuitry configured for acquiring a plurality of physiological measurements from the at least one sensing element during one of a plurality of events respectively corresponding to a plurality of classes;
   a processor configured for deriving a set of data from the plurality of physiological measurements, performing a feature extraction technique on the data set to acquire at least one feature, analyzing the at least one feature, and classifying the data set into the one class corresponding to the one event; and
   a controller configured for performing a function based on the classified data set.

2. The medical system of claim 1, wherein:
   the at least one sensing element comprises a plurality of sensing elements, and the physiological measurements are respectively acquired from the sensing elements; or
   the at least one sensing element is configured for being implanted adjacent the tissue region; or
   the at least one sensing element comprises at least one electrode carried by the at least one medical lead, and the physiological measurements are electrical measurements.

3. The medical system of claim 1, wherein the data set comprises one or both of electrical impedance values and field potential values.

4. The medical system of claim 1, wherein the data set comprises different types of data, wherein the different types of data comprises at least two of an impedance, field potential, evoked potential, pressure, tension, translucence, reflectance, pH, acceleration, chemical, respiration, vascular pulsation, heartbeat, ECG, EKG, and/or EMG, relative lead alignment, absolute lead movement, absolute lead position, and patient posture.

5. The medical system of claim 1, wherein the feature extraction technique is performed using one of a Principal Component Analysis, a Partial Least Square analysis, an Independent Component Analysis, and an artificial neural network.

6. The medical system of claim 1, wherein the at least one feature comprises a plurality of features.

7. The medical system of claim 1, wherein the plurality of events respectively comprises a plurality of different patient postures.

8. The medical system of claim 1, wherein the function is identifying the one event corresponding to the classified data set, and wherein the one event is:
   a posture and/or physical activity of the patient; or
   a migration of the at least one medical lead; or
   a stage of an encapsulation process with respect to the at least one medical lead.

9. The medical system of claim 1, wherein the function is a corrective action.

10. The medical system of claim 9, further comprising:
    at least one electrode carried by the at least one medical lead; and
    analog output circuitry configured for conveying therapeutic electrical energy to the at least one electrode;
    wherein the controller is configured for programming the at least one electrode with a set of neurostimulation parameters prior to performing the function, and the corrective action is modifying the neurostimulation parameter set and reprogramming the at least one electrode with the modified neurostimulation parameter set.

11. The medical system of claim 9, wherein the corrective action is providing a notification message or warning to a user.

12. A medical system configured for performing a medical function in a patient, comprising:
    at least one medical lead configured for being implanted adjacent a tissue region of the patient;
    at least one sensing element;
    monitoring circuitry configured for acquiring a plurality of physiological measurements from the at least one sensing element during one of a plurality of events respectively corresponding to a plurality of classes;
    a processor configured for deriving a set of data from the plurality of physiological measurements, performing a feature extraction technique on the data set to acquire at least one feature, analyzing the at least one feature, and classifying the data set into the one class corresponding to the one event; and
    a controller configured for performing a function based on the classified data set,
    wherein each of the at least one feature has a coefficient, the medical system further comprises memory storing at least one (n−1)-dimensional classification hyperplane that divides an n-dimensional space into a plurality of sub-spaces respectively corresponding to the plurality of different classes, wherein n equals the number of the at least one feature, and wherein the processor is configured for classifying the data set into the one class by recalling the classification hyperplane from the memory, plotting the recalled classification hyperplane and a data point defined by the at least one coefficient in the n-dimensional space, and identifying the sub-space in which the data point is located.

13. A medical system configured for performing a medical function in a patient, comprising:
    at least one medical lead configured for being implanted adjacent a tissue region of the patient;
    at least one sensing element;
    monitoring circuitry configured for acquiring a plurality of physiological measurements from the at least one sensing element during one of a plurality of events respectively corresponding to a plurality of classes;

a processor configured for deriving a set of data from the plurality of physiological measurements, performing a feature extraction technique on the data set to acquire at least one feature, analyzing the at least one feature, and classifying the data set into the one class corresponding to the one event; and a controller configured for performing a function based on the classified data set, wherein, for each of the plurality of events, the monitoring circuitry is configured for acquiring at least one plurality of reference physiological measurements from the at least one sensing element, and the processor is configured for deriving at least one set of reference data respectively from the at least one plurality of reference physiological measurements, performing a feature extraction process on each of the at least one set of reference data to acquire a set of reference features for the respective each reference data set, and defining the plurality of classes from the sets of reference features acquired over the plurality of events.

14. The medical system of claim 13, wherein each set of reference features respectively has a set of coefficients, wherein the at least one plurality of reference physiological measurements for each event comprises at least two pluralities of reference physiological measurements, and the processor is configured for defining the plurality of classes by plotting a plurality of data points in an n-dimensional space, wherein n equals the number of the reference features in each set of reference features, each of the data points being defined by the set of coefficients of the set of reference features, wherein the plurality of classes are defined based on the plotted data points.

15. The medical system of claim 14, wherein processor is configured for defining the plurality of classes by performing a pattern recognition technique on the plotted data points.

16. The medical system of claim 15, wherein the pattern recognition technique is performed using one of machine learning, a classification algorithm, a clustering algorithm, a regression algorithm, and an artificial neural network.

17. The medical system of claim 14, wherein the processor is configured for defining at least one (n−1)-dimensional classification hyperplane that divides the n-dimensional space into a plurality of sub-spaces respectively corresponding to the plurality of classes, the medical system further comprising a memory configured for storing the classification hyperplane, wherein the processor is configured for classifying the data set into the one class by recalling the classification hyperplane from the memory, plotting the recalled classification hyperplane and a data point defined by the at least one coefficient in the n-dimensional space, and identifying the sub-space in which the data point is located.

18. The medical system of claim 13, wherein the processor, for each of the plurality of events, is configured for performing a feature selection technique on a plurality of reference features extracted from each of the at least one set of reference data, and performing a feature selection process that identifies the most significant features that differ between the plurality of events, wherein the acquired set of features includes only the most significant features.

19. The medical system of claim 18, wherein the feature selection technique comprises one of a clustering algorithm, inter-class distance based feature selection, intra-class based feature selection, probabilistic distance based feature selection, correlation based feature selection, consistency based feature selection, and entropy based feature selection.

20. The medical system of claim 13, further comprising:
at least one electrode carried by the at least one medical lead;
telemetry circuitry configured for receiving different user-defined sets of stimulation parameters from an external control device, the different sets of stimulation parameters being respectively correlated to the plurality of events;
analog output circuitry configured for conveying therapeutic electrical energy to the at least one electrode in accordance with the different user-defined sets of stimulation parameters;
wherein the monitoring circuitry is configured for acquiring the at least one plurality of reference physiological measurements from the at least one sensing element in response to the receipt of each of the different user-defined sets of stimulation parameters from the external control device, and wherein the function comprises instructing the analog output circuitry to convey the therapeutic electrical energy to the at least one electrode in accordance with the set of stimulation parameters correlated to the one event.

* * * * *